United States Patent [19]

Roncali et al.

[11] Patent Number: 5,204,424
[45] Date of Patent: Apr. 20, 1993

[54] CONDUCTIVE POLYMERS DERIVED FROM AROMATIC HETEROCYCLIC COMPOUNDS SUBSTITUTED BY AN ETHER-TYPE GROUP

[75] Inventors: Jean Roncali, Les Lilas; Robert Garreau, Sarcelles; Didier Delabouglise, Rouen; Marc Lemaire, Nanterre; Francis Garnier, Champigny, all of France; Etienne Hannecart, Tervueren, Belgium

[73] Assignee: Solvay S.A., Brussels, Belgium

[21] Appl. No.: 280,411

[22] Filed: Dec. 6, 1988

[30] Foreign Application Priority Data

Dec. 7, 1987 [FR] France ................................. 87 17117
Sep. 1, 1988 [FR] France ................................. 88 11572

[51] Int. Cl.$^5$ ........................................... C08F 128/06
[52] U.S. Cl. .................................... 526/256; 252/500; 528/380
[58] Field of Search .................. 526/256; 528/380

[56] References Cited

U.S. PATENT DOCUMENTS

| | | |
|---|---|---|
| 3,574,072 | 4/1971 | Louvar . |
| 4,543,402 | 9/1985 | Traynor . |
| 4,781,443 | 11/1988 | Giles ................................. 528/380 |
| 4,837,096 | 6/1989 | Kimura .............................. 528/380 |
| 4,992,559 | 2/1991 | Kathirgamanathan ............... 549/65 |

FOREIGN PATENT DOCUMENTS

| | | |
|---|---|---|
| 96612 | 12/1983 | European Pat. Off. . |
| 240063 | 10/1987 | European Pat. Off. . |
| 253594 | 1/1988 | European Pat. Off. . |
| 3701495 | 7/1987 | Fed. Rep. of Germany . |

OTHER PUBLICATIONS

Marc Lemaire, et al., "Design of Poly(Thiophene) Containing Oxyalkyl Substituents", *New Journal of Chemistry*, vol. 13, pp. 863–871 (1989).

Robert J. Waltman et al., *Journal of the Electrochemical Society*, "Electroactive Properties of Polyacromatic Molecules", vol. 131, No. 6, pp. 1452–1456 (Jun. 1984).

1046 Journal of the Electrochemical Society 131(1984) Jun., No. 6, Manchester, N.H. "Electroactive Properties of Polyaromatic molecules".

*Primary Examiner*—Christopher Henderson
*Attorney, Agent, or Firm*—Spencer, Frank & Schneider

[57] ABSTRACT

Electrically conductive polymers containing repeat units derived from five-membered aromatic heterocyclic monomers substituted, in the 3 position relative to the heteroatom, by an ether-type substituent linked to the heterocyclic ring by an alkylene radical containing at least two carbon atoms. The invention also relates to certain monomers enabling the above-mentioned conductive polymers to be obtained.

2 Claims, No Drawings

CONDUCTIVE POLYMERS DERIVED FROM AROMATIC HETEROCYCLIC COMPOUNDS SUBSTITUTED BY AN ETHER-TYPE GROUP

The present invention relates to electrically conductive polymers derived from aromatic heterocyclic compounds substituted by an ether-type group.

It relates more particularly to polymers derived from five-membered aromatic heterocyclic compounds containing a heteroatom and substituted in the 3 position by an ether-type substituent linked by an alkylene radical to the heterocyclic ring.

The invention also relates to a process for the manufacture of these polymers.

It also relates to the electrically conductive devices containing these polymers.

Lastly, the invention also relates to the monomers which can be employed for obtaining conductive polymers according to the invention.

Descriptions have already been given of electrodes obtained by electrochemical polymerization, on a conductive substrate, of heterocyclic monomers containing at least one five-membered aromatic heterocyclic ring containing a single heteroatom and substituted by at least one group particularly of alkyl, alkoxy, aryl, substituted aryl, halogen, cyano, amino or dialkylamino type. This monomer may be a derivative substituted in the 3 position, in the 4 position or in the 3 and 4 positions of pyrrole, of thiophene or of furan, or an indole substituted by 1 to 4 groups on the phenyl nucleus (patent application FR-A-2,527,843).

Electrochromic characteristics of polymers derived from these five-membered heterocyclic compounds have also been described, in particular of those derived from pyrrole, from thiophene, from 3-methylthiophene, from 3,4-dimethylthiophene and from 2,2'-dithiophene (F. Garnier et al. Journal of Electroanalytical Chemistry, 148, 1983, pages 299 to 303).

Certain electrical applications, such as the production of devices (display screens, switches, memory components, etc) based on electrochromism (involving a change in the light absorption or transmission properties of the material employed, which is induced by a change in the applied external voltage), of electrodes of rechargeable batteries, of photovoltaic cells, of electrochemical cells, and the like, require conductive polymers with special properties.

These special properties are, in particular, the most complete possible electrochemical reversibility and the highest possible stability of the oxidation-reduction cycle between the oxidized and reduced forms of the polymer-dopant agent system.

Patent Application FR-A-2,596,566 describes a group of polymers having the above-mentioned properties to a certain degree. These polymers contain repeat units derived from 3-alkylthiophenes whose alkyl substituent contains from six to nine carbon atoms.

The present invention is intended to provide a new group of conductive polymers offering the above-mentioned special properties to a still higher degree.

To this end, the invention relates to electrically conductive polymers containing repeat units derived from five-membered aromatic heterocyclic monomers substituted in the 3 position relative to the heteroatom with an ether-type substituent linked to the heterocyclic ring by an alkylene radical containing at least two carbon atoms.

The electrically conductive polymers according to the invention are generally derived from aromatic heterocyclic monomers which can be represented by the general formula below:

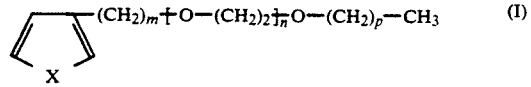

in which:

X denotes an atom or group chosen from sulphur and oxygen atoms and the —NH group, m denotes an integer equal to or greater than 2, n denotes an integer such that $0 \leq n \leq 7$, p denotes an integer such that $0 \leq p \leq 2$, the sum of n and of p being at least equal to 1.

The polymers according to the invention may therefore be derived from thiophene, from furan and from pyrrole, which are substituted in the 3 position.

The substituent is an ether-type group; this group which, as formula (I) shows, may contain one to eight ether groups, and preferably two or three ether groups, separated by ethylene radicals, is linked to the heterocyclic ring by an alkylene radical containing at least two carbon atoms, preferably an ethylene or trimethylene radical.

Polymers derived from monomers corresponding to the general formula (I) which may be mentioned by way of examples are the polymers derived from monomers whose substituent comprises an ether group, such as 2'-methoxy- and 2'-ethoxy-3-ethylthiophene, 2'-methoxy- and 2'-ethoxy-3-ethylfuran and 2'-methoxy- and 2'-ethoxy-3-ethylpyrrole, for example, polymers derived from monomers whose substituent contains two ether groups, such as, for example, 3-(3',6'-dioxaheptyl)- and 3-(3',6'-dioxaoctyl)thiophene, 3-(3',6'-dioxaheptyl)- and 3-(3',6'-dioxaoctyl)furan and 3-(3',6'-dioxaheptyl)- and 3-(3',6'-dioxaoctyl)pyrrole, and polymers derived from monomers whose substituent comprises more than two ether groups, such as, for example, 3(3',6',9'-trioxadecyl)thiophene, -furan and -pyrrole and 3-(4',7',10',13',16',19',22',25'-octaoxahexadodecyl)thiophene, -furan and -pyrrole.

Among all the polymers mentioned above, those preferred are the polymers derived from thiophene substituted in the 3 position and whose substituent contains two ether groups, that is to say the polymers derived from the monomer of formula (I) in which X is a sulphur atom, m has the value of 2 or 3, n has the value of 1 and p has the value of 1 or 0. A compound which is very particularly preferred, especially because it leads to polymers exhibiting exceptional reversibility properties of the oxidation-reduction cycle is 3-(3',6'-dioxaheptyl)thiophene (DHT) (whose polymer is called "PDHT" hereinafter for simplicity).

Another subject of the invention consists of the chemical compounds which can be employed as monomers making it possible particularly to obtain such polymers derived from thiophene substituted in the 3 position and whose substituent contains two ether groups, chosen from the monomers of formula (I) in the case of which m has the value of 2 or 3, n has the value of 1 and p has the value of 1 or 0. Such monomers may be denoted by the general formula (II) below:

(CH$_2$)$_{m'}$—O—(CH$_2$)$_2$—O—(CH$_2$)$_{p'}$—CH$_3$     (II)

in which:
m' denotes the numbers 2 or 3
p' denotes the numbers 0 or 1.

The most particularly preferred monomer in this category is the compound in the case of which m' has the value of 2 and p' has the value of 0, i.e. 3(3',6'-dioxaheptyl)thiophene. DHT is preferably prepared by reacting (2'-(3-thienyl)ethanol with 2-chloroethyl methyl ether in tetrahydrofuran in the presence of sodium hydride.

The temperature at which the reaction is carried out is generally between 5° and 50° C., preferably between 10° and 30° C.

The pressure at which the reaction is carried out is generally between 1 and 4 bars; the reaction is preferably carried out at atmospheric pressure.

The reaction is preferably carried out in the presence of a crown ether and/or of sodium hydride The reaction is preferably carried out under an inert gas atmosphere such as, in particular, argon or nitrogen, and in the presence of a solvent such as, in particular, tetrahydrofuran.

The reaction is carried out in any reactor or apparatus permitting the abovementioned conditions to be combined.

The monomers which can be employed to manufacture the polymers according to the invention may be synthesized according to known methods, for example by reacting 2'-(3-thienyl)-, 2'-(3-furanyl)- and 2'-(3-pyrrolyl)ethanol or the corresponding 3'-substituted 1-propanol with the appropriate oxyalkyl halide.

The preparation of the polymers according to the invention may be carried out by a chemical route, in the presence of oxidizing agents such as FeCl$_3$, for example, or by an electrochemical route. The electrochemical polymerization procedure is preferably employed, generally in an electrolysis cell, using anodic oxidation of the monomer in a polar solvent and in the presence of suitable electrolytes, following conventional methods (see, for example, French Patent Application FR-A-2,527,843 and F. Garnier et al., op. cit.).

According to these methods, the concentration of monomers is generally between $10^{-3}$ and 1 mole per litre of solvent. The temperature at which the process is carried out is generally between 0° and 40° C. and preferably between 4° and 30° C. The pressure at which the process is carried out is generally atmospheric pressure.

The solvents employed are preferably polar solvents capable of dissolving both the monomer and the chosen electrolyte and stable within the range of the voltages which are applied. Examples of solvents which may be employed are acetonitrile, tetrahydrofuran, methylene chloride, nitrobenzene and propylene carbonate.

The electrolytes are generally chosen from conductive salts of formula C$^+$A$^-$ in which C$^+$ is a cation and in which A$^-$ is an anion.

The cation C$^+$ is preferably chosen from alkali metal ions and the R$_4$N$^+$ and R$_4$P$^+$ ions (R being an alkyl radical such as, for example, the ethyl and butyl The anion A$^-$ is preferably chosen from the ClO$_4$, AsF$_6^-$, SbF$_6^-$, SO$_4^{2-}$, C$_6$H$_5$COO$^-$, C$_6$H$_5$SO$_3^-$, BF$_4^-$, PF$_6^-$ and CF$_3$SO$_3^-$ ions.

Typical electrolytes are, for example, fluorophosphates such as tetrabutylammonium hexafluorophosphate, fluoroborates such as tetraethylammonium tetrafluoroborate and perchlorates such as lithium perchlorate and tetrabutylammonium perchlorate.

The electrolyte concentration is generally between $10^{-3}$ and 1 mole per litre of solvent.

The polymerizatin of monomers according to the invention may be carried out in an electrochemical cell operated under either constant-voltage or constant-current conditions.

In the first case, (constant-voltage control), the cell comprises, in addition to the external current source, three electrodes including a reference electrode or voltage control.

During the electrolysis a layer of polymer is deposited onto the conductive member employed as the anode of the electrolysis cell. This anode may be made of a noble metal such as gold or platinum, or of another metal, such as copper, plated with gold or platinum, titanium, nickel, or of conductive glass (tin oxide, indium-tin oxides). After the electrolysis, an electrode will therefore be available, consisting of a conductive body coated with a polymer film adhering thereto and containing a certain proportion of the anion originating from the electrolyte. The polymer and the anion thus form a charge-transfer complex. The chemical composition of the polymer film may be repreradicals). sented by the empirical formula (M$^+$Ay$^-$)$_n$ where M$^+$ denotes the monomer, A$^-$ the anion or counterion, y the proportion of anion in the polymer, expressed in monomer units (that is to say the degree of doping) which, in the case of the polymers of the invention, may reach the value of 0.5, and n the degree of polymerization, which is generally impossible to determine easily, bearing in mind the insoluble nature of the polymer.

Since the electrochemical polymerization of the monomer takes place on the anode of the electrolysis cell, an electrode coated with a cation-doped polymer cannot be obtained directly.

To obtain a cathode of this kind, the anode obtained as above may be used and may be subjected to a double reduction. A first electrochemical reduction is possible just after the polymerization by leaving the anode in the electrolysis cell and discharging the cell. This discharge causes the anions "doping" the polymer to be extracted. A second reduction may then be carried out under an inert atmosphere, either by a chemical route or by an electrochemical route. The chemical route consists in immersing the polymer in a solution containing the desired cations. Thus, in order to obtain a polymer "doped", for example, with Li$^+$, Na$^+$ or K$^+$ cations ("n" type doping to which the polymers according to the invention, especially PDHT, are particularly well-suited), use may be made, for example of a solution of naphthalenelithium, or naphthalenesodium or of naphthalenepotassium in tetrahydrofuran. The electrochemical route generally consists in placing the electrode as a cathode in an electrolysis cell containing the desired cations in solution. The cations may be, for example, alkali metal ions such as those mentioned above, preferably the Li$^+$ or K$^+$ cations or complex ions such as (Bu)$_4$N$^+$ or (Et)$_4$N$^+$ originating from an electrolyte (preferably LiClO$_4$, KPF$_6$, (Bu)$_4$NClO$_4$ and (Et)$_4$NClO$_4$) in solution in a solvent such as acetonitrile, tetrahydrofuran or propylene carbonate. The electrolyte concentration in the solution is generally between $10^{-3}$ and 1 mole per 1 litre of solvent.

The conductive polymers according to the invention exhibit a combination of quite remarkable properties which are, chiefly an exceptional reversibility and stability of the oxidation-reduction cycle between their oxidized and reduced forms; thus, in particular, in the case of the preferred polymer (PDHT) the stability of the oxidation-reduction cycle is such that it can undergo up to $0.5 \times 10^7$ cycles while still retaining 90% of the initial charge;

a considerable change in the spectral characteristics which is obtained with a very low voltage change, which makes their use as an electrochromic material advantageous and economical;

good electrical conductivity, generally between $10^1$ and $10^2$ S cm$^{-1}$;

high absorptions in the near infrared and high frequency radiation region.

These remarkable properties of the conductive polymers according to the invention make them particularly capable of being used for the production of electroconductive devices whose operating principle is based on these properties, and which also form a subject of the present invention.

By way of nonlimiting examples of electrically conductive devices containing conductive polymers derived from the substituted aromatic heterocyclic monomers according to the invention, there may be mentioned:

electrochemical energy storage devices such as rechargeable or otherwise accumulator and cell batteries whose anodes (or cathodes) consist of electrodes coated with films of the said polymers doped with anions (or cations);

electrochromic devices based on the change in the optical spectrum of the said polymers according to their electrochemical state, which is observed during the oxidation and reduction cycles of the polymer films deposited on the anodes (or the cathodes) of these devices during the charge and the discharge; by way of examples of such electrochemical devices there may be mentioned display screens, optoelectronic devices, memories and optical switches.

The invention is illustrated by the following example, without any limitation being implied.

EXAMPLE

A. Preparation of the monomer 110 mmol Of 60% strength NaH dispersed in oil and 200 mg of a crown ether marketed by Aldrich under the name 18 C 6 are added to a solution of 100 mmol of 2'-(3-thienyl)ethanol (supplied by Janssen Chemica) in 100 ml of tetrahydrofuran. The suspension is maintained at 20° C. for 2 hours and 200 mmol of 2-chloroethyl methyl ether sold by Aldrich are then added over 15 minutes and the suspension is refluxed for 8 hours. The suspension, brought back to 20° C., is treated with HCl. The organic phases are washed with water to neutrality and are then evaporated down under vacuum. The crude product is purified by chromatography and then distilled under vacuum.

B. Synthesis of the polymer

The synthesis of the polymer is carried out in a single-compartment thermostated cell containing:

$2 \times 10^{-1}$ mole of monomer prepared as in A, $3 \times 10^{-2}$ mole of tetrabutylammonium hexafluorophosphate (supplied by Fluka), 25 ml of distilled nitrobenzene.

The polymer deposits are produced at 5° C., under argon atmosphere, after degassing the solution by bubbling argon. For the electrochemical characterizations the polymer is deposited onto solid platinum electrodes with a surface area of 0.07 and 0.7 cm$^2$, polished between each experiment. The quantities of charges employed vary from 20 to 100 mC/cm$^2$, which corresponds to thicknesses of between 600 and 3000 Å. The cathode consists of a platinum wire and the reference electrode is a saturated calomel electrode.

The polymer films intended for spectroscopic studies and for conductivity measurements have been synthesized under the same conditions, the working electrode consisting of a sheet of conductive glass and the cathode of an aluminium plate. The depositions are carried out under constant current conditions with current densities of between 2 and 5 mA/cm$^2$. The spectroelectrochemical characterizations have been performed in a spectrometry cell with an optical path of 1 cm, equipped with a cathode consisting of a platinum wire and a reference electrode consisting of a silver wire.

The polymer films intended for the long-term stability tests for redox reversibility have been synthesized on a 0.7 cm$^2$ solid platinum electrode. This electrode is then placed in a cell equipped with a circular counter-electrode consisting of a platinum wire and of a reference electrode consisting of a silver wire. The cell is equipped with an optical window permitting the measurement of the response time by reflection with the aid of a helium-neon laser ($\lambda = 632.8$ nm) and of a GaAsP photodiode. The redox cycling is carried out in an electrolytic medium consisting of propylene carbonate containing $5 \times 10^{-1}$ mole of anhydrous lithium perchlorate.

The "n" doping tests were carried out in propylene carbonate containing $5 \times 10^{-2}$ mole of tetraethylammonium perchlorate.

The electrochemical properties of the polymers have been measured using the cyclic volt-ampere plot recorded by means of a PAR model 173 potentiostat and using the recorded intensity peaks. The anode wave includes two oxidation peaks: 0.4 and 0.8 V/SCE (reference calomel electrode). In the case of these two systems the relationship $I_{Pa}/I_{Pc}$ between the intensities of the oxidation ($I_{Pa}$) and reduction ($I_{Pc}$) current is approximately 1.

In the case of the first system, the stability of the redox reversibility, expressed as the percentage of charges which are still exchanged, is:

100% after $0.65 \times 10^6$ cycles
96% after $1.5 \times 10^6$ cycles
92% after $3.25 \times 10^6$ cycles
90% after $0.5 \times 10^7$ cycles The "n" doping of the polymer is evaluated by an observation of a cathodic system which is reversible between $-1.7$ and $-2.2$ V/Ag.

The optical and spectroscopic characteristics are the high absorption in the red (absorption band at $\lambda = 600$ nm) of the polymer and the very weak absorption of the dedoped polymer beyond 600 nm.

On the other hand, the doped polymer has a strong absorption band in the far red and the near infrared.

This phenomenon lies at the origin of a special electrochromic behaviour. In fact, when the change in the intensity of the reflection of a laser beam (helium-neon: $\lambda = 632.8$ nm) on a polymer film subjected to voltage pulses is analyzed, two stable states are observed in the applied voltage values up to 0.7 V/Ag whereas, beyond this, only a single stable state is obtained. This threshold effect phenomenon can be used for applications in opto-electronics.

We claim:

1. An electrically conductive polymer containing repeat units derived from 3-(3',6'-dioxaheptyl) thiophene prepared by electrochemical polymerization by an anodic oxidation in a polar solvent in the presence of an electrolyte.

2. An electrically conductive polymer containing repeat units derived from 3-(3',6'-dioxaheptyl) thiophene.

* * * * *

UNITED STATES PATENT AND TRADEMARK OFFICE
CERTIFICATE OF CORRECTION

PATENT NO. : 5,204,424
DATED : April 20, 1993
INVENTOR(S) : Jean RONCALI et al.

It is certified that error appears in the above-identified patent and that said Letters Patent is hereby corrected as shown below:

On the title page: Item [54] and Column 1, line 1, should read

CONDUCTIVE POLYMERS DERIVED FROM 3-(3',6'-DIOXAHEPTYL)

THIOPHENE -- .

Signed and Sealed this

Third Day of May, 1994

Attest:

BRUCE LEHMAN

Attesting Officer Commissioner of Patents and Trademarks